(12) United States Patent
Castillo et al.

(10) Patent No.: US 9,453,168 B2
(45) Date of Patent: *Sep. 27, 2016

(54) SYNTHESIS OF ACIDIC SILICA TO UPGRADE HEAVY FEEDS

(71) Applicant: Board of Regents, The University of Texas System, Austin, TX (US)

(72) Inventors: Karina Castillo, San Juan, TX (US); Jason Parsons, Edinburg, TX (US); Russell R. Chianelli, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/558,156

(22) Filed: Dec. 2, 2014

(65) Prior Publication Data

US 2015/0090633 A1 Apr. 2, 2015

Related U.S. Application Data

(62) Division of application No. 13/910,195, filed on Jun. 5, 2013, now Pat. No. 8,900,447, which is a division of application No. 12/814,012, filed on Jun. 11, 2010, now Pat. No. 8,480,881.

(60) Provisional application No. 61/265,236, filed on Nov. 30, 2009, provisional application No. 61/186,178, filed on Jun. 11, 2009.

(51) Int. Cl.
*C10G 45/00* (2006.01)
*C10G 45/24* (2006.01)
*C10G 1/00* (2006.01)
(Continued)

(52) U.S. Cl.
CPC ............ *C10G 45/24* (2013.01); *C07D 333/76* (2013.01); *C10G 1/00* (2013.01); *C10G 1/002* (2013.01); *C10G 45/28* (2013.01); *C10G 45/30* (2013.01); *C10L 1/04* (2013.01);
(Continued)

(58) Field of Classification Search
CPC ............................. C10G 45/00; C10G 45/24
USPC ............................. 208/208 R, 209, 214, 390
See application file for complete search history.

(56) References Cited

U.S. PATENT DOCUMENTS

| | | |
|---|---|---|
| 4,329,221 A | 5/1982 | Farcasiu et al. |
| 4,444,655 A | 4/1984 | Shiroto et al. |

(Continued)

OTHER PUBLICATIONS

Al-Shahrani, et al., "Desulfurization of Diesel via the H2O2 Oxidation of Aromatic Sulfides to Sulfones using a Tungstate Catalyst," Applied Catalysis B: Environmental, (Jan. 2007), 73:311-316.

(Continued)

*Primary Examiner* — Ellen McAvoy
(74) *Attorney, Agent, or Firm* — Kermit D. Lopez; Luis M. Ortiz; Ortiz & Lopez, PLLC

(57) ABSTRACT

A method and a product made by treating a sulfur-containing hydrocarbon heavy feed, e.g., heavy crude asphaltene reduction is disposed herein. The method comprises the steps of: mixing the sulfur-containing hydrocarbon heavy feed with a hydrogen donor solvent and an addled silica to form a mixture and oxidizing the sulfur in the mixture at a temperature between 50° C. and 210° C. wherein the oxidation lowers the amount sulfur in the sulfur-containing hydrocarbon heavy feed by at least 90%.

21 Claims, 6 Drawing Sheets

(51) Int. Cl.
- *C07D 333/76* (2006.01)
- *C10G 45/30* (2006.01)
- *C10G 45/28* (2006.01)
- *C10L 1/04* (2006.01)

(52) U.S. Cl.
CPC ...... *C10G 2300/107* (2013.01); *C10L 2200/0438* (2013.01); *C10L 2270/026* (2013.01); *C10L 2290/24* (2013.01)

(56) References Cited

U.S. PATENT DOCUMENTS

| | | |
|---|---|---|
| 4,511,458 A | 4/1985 | Billon et al. |
| 4,937,218 A | 6/1990 | Ramirez de Aqudelo et al. |
| 5,024,750 A | 6/1991 | Sughrue, II et al. |
| 6,383,974 B1 | 5/2002 | Ishida et al. |
| 6,547,957 B1 | 4/2003 | Sudhakar et al. |
| 6,902,664 B2 | 6/2005 | Timken |
| 6,995,112 B2 | 2/2006 | Timken et al. |
| 7,381,320 B2 | 6/2008 | Iqbal et al. |
| 7,465,395 B2 | 12/2008 | Carbonell et al. |
| 7,476,309 B2 | 1/2009 | Abe et al. |
| 7,566,394 B2 | 7/2009 | Koseoglu |
| 7,594,992 B2 | 9/2009 | Timken et al. |
| 7,700,515 B2 | 4/2010 | Acerman et al. |
| 7,713,408 B2 | 5/2010 | Breivik et al. |
| 7,790,018 B2 | 9/2010 | Khan |
| 7,922,894 B2 | 4/2011 | Plantenga et al. |
| 7,964,090 B2 | 6/2011 | Iqbal |
| 8,201,445 B2 | 6/2012 | Carbonell et al. |
| 8,480,881 B2 * | 7/2013 | Castillo ............ C10G 1/00 208/209 |
| 8,900,447 B2 * | 12/2014 | Castillo ............ C10G 1/00 208/309 |
| 2004/0256293 A1 | 12/2004 | Abe et al. |
| 2007/0267327 A1 | 11/2007 | Boakye |
| 2010/0038287 A1 | 2/2010 | Mienegassi de Almeida et al. |
| 2012/0055845 A1* | 3/2012 | Bourane ............ C10B 55/00 208/90 |
| 2012/0074040 A1* | 3/2012 | Koseoglu ........... C10G 27/12 208/97 |

OTHER PUBLICATIONS

Babich, I. V., et al., "Science and Technology of Novel Processes for Deep Desulfurization of Oil Refinery Streams: A Review," Fuel (2003) 82:607-631.

Brinker, et al., "Sol-Gel Transition in Simple Silicates," Journal of Non-Crystalline Solids (1982) 48:47-64.

Caero, et al., "Oxidative Desulfurization of Synthetic Diesel Using Supported Catalysts Part II. Effect of Oxidant and Nitrogen-Compounds on Extraction-Oxidation Process," Catalysis Today (Jul. 2006) 116:562-568.

Chan, et al., "Superoxides: Alternative Oxidants for Oxidative Desulfurization Process," Energy & Fuels (Jul. 2008) 22:3326-3328.

Ciclosi, et al., "Oxidation of Thiophene Derivatives with H2O2 in Acetonitrile Catalyzed by [Cp*2M2O5] (M=Mo,W): A Kinetic Study," Organometallics (Apr. 2008) 27:2281-2286.

Cojocariu, et al., "Non-Hydrolytic Synthesis of Mesoporous Silica-Titania Catalysts for the Mild Oxidation of Sulfur Compounds with Hydrogen Peroxide," Chem. Comm. (Sep. 2008) 5357-5359.

Dumount, et al., "Oxidation of Dibenzothiophene by a Metal-Oxide-Aldehyde System," Catalysis Today (Oct. 2008) 130:195-198.

Gordon, et al., "Partition Chromatography in the Study of Protein Constituents," Biochemical Journal (1943) 37:79-86.

Huang, et al., "Effect of HCl in a Two-Step Sol-Gel Process Using TEOS," Journal of Non-Crystalline Solids (Jul. 1999) 258:234-238.

Huang, et al., "Direct Synthesis of Mesoporous TiO2 and its Catalytic Performance in DBT Oxidative Desulfurization," Microporous and Mesoporous Materials (May 2008) 116:378-385.

Kim, et al., "Ultra-Deep Desulfurization and Denitrogenation of Diesel Fuel by Selective Adsorption over Three Different Absorbents: A Study on Adsorptive Selectivity and Mechanism," Catalysis Today (Nov. 2005) 111:74-83.

Kronfeld, Louis R., Sass, Ronald L., "Crystal Structure of Dibenzothiphene Sulfone," William Marsh Rice Univ., Houston, TX, USA, Acta Crystallographica, Section B: Structure Crystallography and Crystal Chemistry (Jun. 1967) 24(Pt. 7):981-982.

Maciuca, et al., "V-, Mo- and W-Containing Layered Double Hydroxides as Effective Catalysts for Mild Oxidation of Thioethers and Thiophenes with H2O2," Catalysis Today (Jun. 2008) 138:33-37.

Margaca, et al., "Small Angle Neutron Scattering Study of Silica Gels: influence of pH," Journal of Non-Crystalline Solids (Jul. 1999) 258:70-77.

Mondal, et al., "Oxidation of Sulfur Components in Diesel Fuel using Fe-TAML Catalysts and Hydrogen Peroxide," Catalysis Today (Jul. 2006) 116:554-561.

Ramirez-Verduzco, et al., "Solvent Effect in Homogeneous and Heterogeneous Reactions to Remove Dibenzothiophene by and Oxidation-Extraction Scheme," Ind. Eng. Chem. Res. (2008) 47:5353-5361.

Sampanthar, et al., "A novel Oxidation Desulfurization Process to Remove Refractory Sulfur Compounds from Diesel Fuel," Applied Catalysis B: Environmental (Oct. 2005) 63:85-93.

Shen, et al., "Desulfurization by Oxidation/Adsorption Scheme over Ti3(PW12O40)4 Catalysts," Petroleum Science and Technology (2008) 26:2182-2193.

Shokrolahi, et al., "Carbon-Based Solid Acid Catalyzed Highly Efficient Oxidations of Organic Compounds with Hydrogen Peroxide," Catalysis Communications (Sep. 2007) 9:859-863.

Song, C., Ma, X., "New Design Approaches to Ultra-Clean Diesel Fuels by Deep Desulfurization and Deep Dearomatization," Applied Catalysis B: Environmental (Jan. 2002) 41:207-238.

Ukkirapandian, et al., "Oxidation of Dibenzothiophene and Desulphurization of Diesel," Petroleum Science and Technology (2008) 26:423-435.

Venkateshwar Rao, et al., "Oxidative Desulfurization of HDS Diesel Using the Aldehyde/Molecular Oxygen Oxidation System," Energy & Fuels (2007) 21:3420-3424.

Wang, et al., "Gold Nanoparticles Supported on Manganese Oxides for Low-Temperature CO Oxidation," Applied Catalysis B: Environmental (Oct. 2008) 88:204-212.

Zali, et al., "Carbon-based Solid Acid Catalyzed Highly Efficient Selective Oxidations of Sulfides to Sulfoxides or Sulfones with Hydrogen Peroxide," Acta. Chim. Slov. (2008) 55:257-260.

Zolfigol, et al., "Chemo and Homoselective Catalytic Oxidation of Sulfides to Sulfoxides with Support Nitric Acid on Silica Gel and Ply Vinyl Pyrrolidone (PVP) Catalyzed by KBr and/or NaBr," Catalysis Communications (Feb. 2008) 9:1739-1744.

* cited by examiner

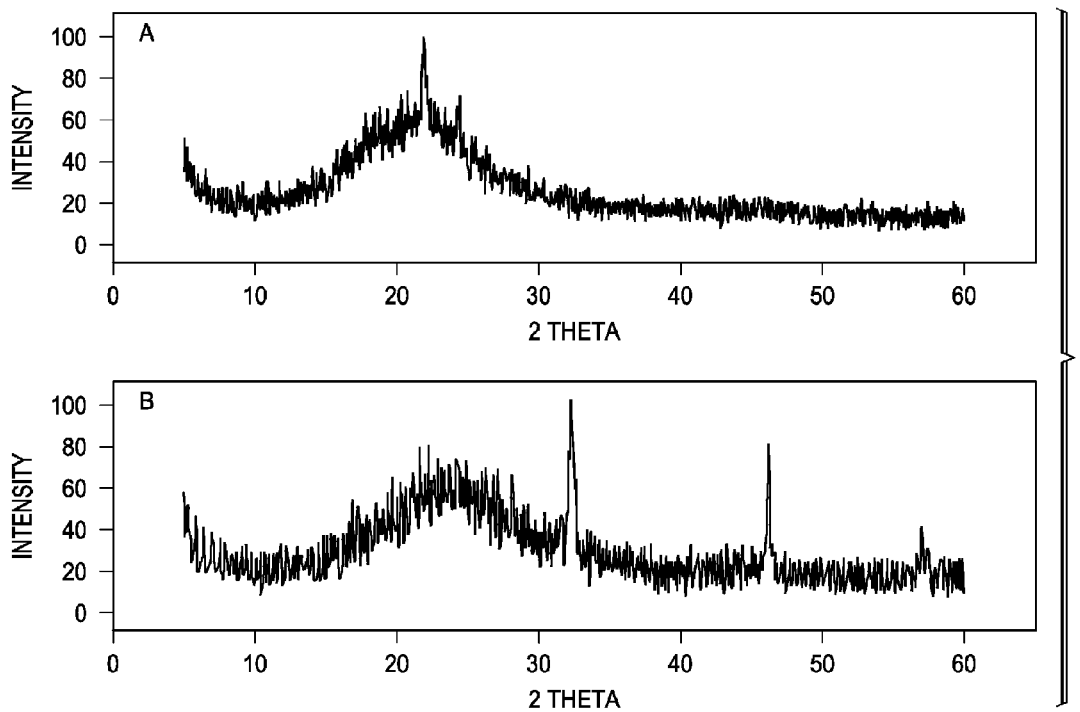
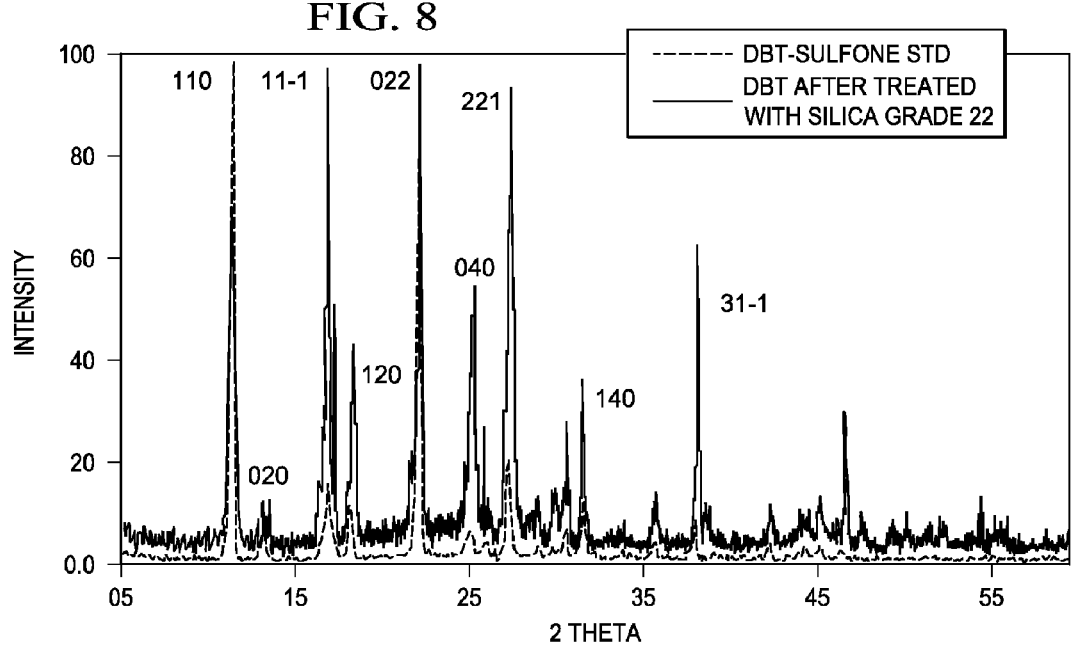

SYNTHESIS OF ACIDIC SILICA TO UPGRADE HEAVY FEEDS

CROSS-REFERENCE TO RELATED APPLICATIONS

This application is a divisional of U.S. patent application Ser. No. 13/910,195, filed Jun. 5, 2014, entitled "SYNTHESIS OF ACIDIC SILICA TO UPGRADE HEAVY FEEDS;" which claims priority to U.S. Provisional Application Ser. Nos. 61/186,178 and 61/286,238 filed Jun. 11, 2009 and Nov. 30, 2009, respectively, and U.S. patent application Ser. No. 12/814,012 filed Jun. 11, 2010, the disclosures of which are incorporated herein by reference.

FIELD OF THE INVENTION

Embodiments relate to the field of oxidative catalysis, and more particularly, to the use of a dibenzothiophene (DBT) model reaction system to investigate the oxidation properties of silica gel ($SiO_2$).

BACKGROUND

Without limiting the scope of the disclosed example embodiment, the patent application its background is described in connection with the oxidative properties of silica gel and related compounds.

Developed countries are setting new standards for the allowable amount of sulfur in diesel. By 2009 the allowable amount of sulfur will be 15/10 ppm in diesel fuel[1]. Currently, hydrodesulfurization processes are utilized to remove sulfur from fuels. These processes involve high temperatures from 350° C.-700° C. and high pressures of about 3-5 MPa of $H_2$[2] depending on the quality of the oil.

U.S. Pat. No. 7,713,408 issued to Breivik and Knudsen (2010) teaches a process for the catalytic hydrotreating of a hydrocarbon feed stock containing silicon compounds comprising the steps of contacting the feed stock in presence of hydrogen with a first hydrotreating catalyst being arranged in at least two reactors being connected in series at an outlet temperature of up to 410° C. to reduce content of the silicon compounds in the feed stock; cooling of the feed stock such treated to a temperature of between 280° C. and 350° C.; and contacting the cooled feed stock with a second hydrotreating catalyst at conditions being effective in reduction of sulfur compound and nitrogen compound concentration.

From an economic and environmental point of view, it would be more suitable if low-temperature and low-pressure systems could be developed to remove sulfur from fuels. Higher temperature and pressure processes decrease the catalyst life and involves higher $H_2$ consumption and thus, higher costs. In addition, high-temperature and high-pressure processes result in the generation of $H_2S$, a highly toxic compound.

Another reason why if is important to find another method to remove sulfur is because sulfur compounds such as methyl ethyl dibenzothiophene, 4-methyl dibenzothiophene, 3 methyl dibenzothiophene and others are poorly reactive under the hydrodesulfurization process[3-5]. In order to decrease the levels of sulfur in gasoline and meet environmental regulations it is necessary to eliminate these sulfur compounds from crude oils.

There are other promising techniques for the removal of sulfur, such as bio-desulphurization, extraction, selective adsorption, extraction with ionic liquids, phase transfer catalysts, and oxidative desulfurization to remove sulfur compounds[6-8]. Most of these techniques utilize oxidizing agents such as $NO_2$, $H_2O_2$ and ter-butyl-hydroperoxide[9-10]. One advantage of using these techniques is that sulfur can be removed at relatively low temperatures and atmospheric pressure. However, the catalysts utilized in the aforementioned techniques, are made of ruthenium and other expensive metals. In addition, the constant use of strong oxidizing agents such as hydrogen peroxide can also become expensive.

U.S. Pat. No. 4,329,221 issued to Farcasiu et al. (1982) provides a process for reducing the metal, sulfur, and nitrogen content of petroleum residual oils. The process involves contacting a mixture of hydrocarbon feedstock and hydrogen-donor solvent with a catalyst composition comprising a naturally occurring porous metal ore such as manganese nodules.

In addition to the high temperature and high pressure catalysts currently available, there are other techniques for the removal of sulfur, such as, selective adsorption, extraction with ionic liquids, phase transfer catalysts, and oxidative desulfurization to remove these sulfur compounds[6-8]. For example, $Mo/Al_2O_3$ catalysts have been used in the oxidative desulfurization (OD) process using hydrogen peroxide as the oxidizing reagent, it has also been proposed to use $Ti_3(PW_{12}O_{40})_4$ catalyst, which also requires the use $H_2O_2$[9-10]. There has been research in oxidative desulfurization using decalin solution with sulfur compounds of dibenzothiophene (DBT), where Bu hydroperoxide (TBHP) was used as the oxidant and molybdenum oxide catalyst supported on resins was used as catalyst[11]. Superoxides for instance, potassium superoxide, has been demonstrated as an alternative oxidant for the oxidative desulfurization process[12]. For model compounds of benzothiophene, dibenzothiophene, and a number of selected diesel oil samples, sulfur removal greater than 90% and as high as 99% has been accomplished using potassium superoxide[12].

U.S. Patent Publication No. 20100038287 (Menegassi et al., 2010) relates to a process for removing organic silicon compounds from hydrocarbon streams by contact with an adsorbent and hydrogen. The adsorbent is composed of lamellar double hydroxides and group VI-B or group VIII hydrogenating metal. More specifically, the process of the present Invention involves a stage of activation for formation of the lamellar double hydroxide, and maintaining the phase of lamellar double hydroxide by adding water.

Peroxides have been used to oxidize DBT as have oxidizing solvents such as aldehydes and carboxylic acid[35-36]. For example, it has been reported the use of a surfactant-type decatungstates for the oxidation of DBT. This reaction requires hydrogen peroxide[24]. Also, oxidative desulfurization of dibenzothiophene catalyzed by Keggin-type $H_3PMo_{12}O_{40}$ and $Na_3PMo_{12}O_4$ using hydrogen peroxide as the oxidizing agent is found in the literature[25].

SUMMARY

The disclosed embodiments overcome overcomes these and other problems in the prior art, and describe novel compositions and methods for making and using acidic silica (pH 0-4) to oxidize dibenzothiophene (DBT) to dibenzothiophene sulfone under reflux conditions between 50° C. and 210° C. in the presence of a hydrogen donor solvent. In addition, the combination of silica with gold speeds up the oxidation process. The catalysts were characterized using x-ray diffraction (XRD), infrared spectroscopy and x-ray fluorescence (XRF). Infrared spectroscopy was also used to follow the oxidation of DBT to DBT sulfone.

One example embodiment includes a method of treating a sulfur-containing hydrocarbon heavy feed. Such an example embodiment includes the step of mixing the sulfur-containing hydrocarbon heavy feed with a hydrogen donor solvent and an acidified silica to form a mixture followed by oxidizing the sulfur in the mixture with an oxidant at a temperature between 50° C. and 210° C., wherein the oxidation lowers the amount of sulfur in the sulfur-containing hydrocarbon heavy feed by at least 90%. The heavy feeds can include, for example, comprise asphaltene, tar sands, bitumens, heavy petroleum or mixtures thereof. In one aspect, the hydrogen donor solvent is selected from a group comprising hydrogen, natural petroleum, bases, alcohols, decahydronaphthalene, and tetrahydronaphthalene. The oxidant is air or a mixture of air and $O_2$. In another aspect, the acidified silica has a pH in the range from 0 to 2. In yet another aspect, the silica comprises an amorphous silica and/or a silica gel. In one aspect, the temperature for oxidizing the mixture is 120° C. to 160° C. In another aspect, the temperature for oxidizing the mixture is 120° C., 125° C., 130° C., 135° C., 140° C., 145° C., 150° C., 155° C., and 160° C. In another aspect of an example embodiment, the method can include the step of adding a reduced noble metal catalyst or a mixture of a noble metal and one or more acidic catalysts, wherein the acidic catalysts comprise zeolites, silica, alumina or combinations thereof. The noble metal catalyst comprises reduced gold, platinum, silver, palladium, or mixtures thereof. Another example embodiment is directed towards the solvents comprising at least one of decalin, tetralin, toluene, heptane, and dodecane. In another example embodiment, the final sulfur concentration in the hydrocarbon heavy feed has less than 1,000, 500, 250, 200, 100, 50 or 10 ppm sulfur after treatment. Yet another example embodiment can include a treated hydrocarbon feed made by the method described herein.

In another embodiment, a method of treating a sulfur-containing hydrocarbon heavy feed can include the steps of: mixing the sulfur-containing hydrocarbon heavy feed with a hydrogen donor solvent and an amorphous acidified silica to form a mixture wherein the hydrocarbon heavy feed comprises asphaltene, tar sands, bitumens, heavy petroleum or mixtures thereof, and oxidizing the sulfur in the mixture at a temperature between 120° C. and 210° C., wherein the oxidation lowers the amount sulfur in the sulfur-containing hydrocarbon heavy feed to less than 1,000 ppm sulfur. In one aspect, the hydrogen donor solvent is selected from a group comprising hydrogen, natural petroleum, bases, alcohols, decahydronaphthalene, and tetrahydronaphthalene. In one aspect, the acidified silica ahs a pH in the range from 0 to 2. In yet another aspect, the silica comprises a silica gel.

In another example embodiment the temperature for oxidizing the mixture is 120° C. to 160° C., and then oxidation is carried out in air or a mixture of air and $O_2$. Another aspect of the disclosed embodiments can further include adding a reduced noble metal catalyst or a mixture of a noble metal and one or more acidic catalysts, wherein the acidic catalysts comprise zeolites, silica, alumina or combinations thereof. In yet another aspect reduced gold, platinum, silver, palladium or mixtures thereof. In certain aspects, the silica comprises reduced gold, platinum, silver, palladium or mixtures thereof. One aspect of the disclosed embodiments is directed towards the solvents comprising at least one of decalin, tetralin, toluene, heptane, and dodecane. In a specific aspect, the heavy feed comprises asphaltene.

In yet another embodiment, a method of treating a sulfur-containing hydrocarbon heavy feed can include asphaltenes, tar sands, bitumens, heavy petroleum or mixtures thereof, and can include the steps of: mixing the sulfur-containing hydrocarbon heavy feed comprising asphaltenes with a natural petroleum solvent and an acidified silica to form a mixture; oxidizing the sulfur in the mixture in air or in a mixture of air and $O_2$ at a temperature between 120° C. and 210° C., wherein the oxidation lowers the amount sulfur in the sulfur-containing hydrocarbon heavy feed to less than 100 ppm sulfur; and recovering the acidified silica.

Yet another example embodiment involves a method of treating a sulfur-containing hydrocarbon heavy feed comprising the steps of: mixing the sulfur-containing hydrocarbon heavy feed with a hydrogen donor solvent and an acidified silica to form a mixture; oxidizing the sulfur in the mixture at a temperature between 50° C. and 210° C., wherein the oxidation lowers the amount sulfur in the sulfur-containing hydrocarbon heavy feed by at least 90%; and recovering the acidified silica by water extraction and/or a heavy feed treated by the above method. In one aspect, the sulfur-containing hydrocarbon heavy feed comprises asphaltenes, tar sands, bitumens, heavy petroleum or mixtures thereof.

In one example embodiment, a method of extracting sulfur from an oxidized hydrocarbon feed can include the steps of: (i) mixing a solution comprising a sulfur containing oxidized hydrocarbon feed, an acidified silica, a hydrogen donor solvent, any unreacted materials and reaction by-products with one or more polar organic solvents, (ii) allowing the sulfur containing oxidized hydrocarbon feed to migrate to the polar organic solvent phase, and (iii) removing the one or more polar organic solvents by evaporation to recover the sulfur. The hydrocarbon heavy feed of the present invention comprises asphaltenes, tar sands, bitumens, heavy petroleum or mixtures thereof. In one aspect the hydrogen donor solvent is selected from a group comprising hydrogen, natural petroleum, bases, alcohols, decahydronaphthalene, and tetrahydronaphthalene. In another aspect the acidified silica has a pH range from 0 to 2 and further comprises an amorphous silica or a silica gel. In yet another aspect, the polar organic solvent is selected from ethanol, methanol, n-propanol, isopropanol, n-butanol, formic acid, acetic acid, 1,4-dioxane, THF, dichloromethane, acetone, acetonitrile, DMF, DMSO, or any combinations thereof. In a further aspect, an example embodiment describes a sulfur extracted from a hydrocarbon feed by the method of the disclosed embodiments.

Another example embodiment is directed towards a method of reducing asphaltene content in a crude oil comprising the steps of: mixing the crude oil with an organic solvent and one or more silica-noble metal nanoparticles to form a mixture, refluxing the mixture to obtain a solid residue comprising asphaltenes, and filtering the refluxed mixture to recover the asphaltene in the solid residue and the final crude oil with reduced asphaltene content in the filtrate. In one aspect the noble metals comprise gold, platinum, silver, and palladium or mixtures thereof. In another aspect the final crude oil has less than 11%, 10%, 9%, 8%, 7%, 6%, 5%, 4%, and 3% of asphaltene after treatment. Yet another aspect describes a treated crude oil with reduced asphaltene content made by the method of the disclosed embodiments.

In yet another example embodiment, invention provides a method for mid-distillate upgradation and for sulfur removal in a fuel can include the steps of: (i) mixing the fuel with a hydrogen donor solvent and an acidified silica to form a mixture and (ii) oxidizing the sulfur in the mixture in air or a mixture of air and $O_2$ at a temperature between 50° C. and 210° C. The fuels that are treated by the method of the present invention comprise diesel, heavy petroleum, asphaltene, tar sands, bitumens, or mixtures thereof. In one aspect of the disclosed embodiments, the hydrogen donor solvent can be selected from the group consisting of hydrogen, natural petroleum, bases, alcohols, decahydronaphthalene, and tetrahydronaphthalene. In another aspect, the acidified silica has a pH range from 0 to 2 and further comprises an amorphous silica or a silica gel. The temperature for oxidizing the mixture as described in another aspect of the method of the disclosed embodiments is 120'C to 160° C. In yet another aspect, the disclosed can further include the step of adding a reduced noble metal catalyst or a mixture of a noble metal and one or more acidic catalysts, wherein the acidic catalysts comprise zeolites, silica, alumina or combinations thereof.

In one aspect of the disclosed embodiments, the method includes adding reduced gold, platinum, silver, and palladium metal nanoparticles or mixtures thereof. In another aspect the silica comprises reduced gold, platinum, silver, and palladium particles or mixtures thereof. In yet another aspect the solvents comprise at least one of decalin, tetralin, toluene, heptane, and dodecane. In a specific aspect the method lowers the amount sulfur in the fuel by at least 90%. The fuel after the treatment by the method of the present invention has less than 1,000, 500, 250, 200, 100, 50 or 10 ppm sulfur. Finally, one or more of the disclosed example embodiments describes a fuel made according to the disclosed method.

BRIEF DESCRIPTION OF THE FIGURES

For a more complete understanding of the features and advantages of the present invention, reference is now made to the detailed description: of the invention along with the accompanying figures and in which:

(FIG. 1A) DBT after silica grade 22 run at 160° C. (FIG. 1B) DBT after lab synthesized silica at pH 0-2, (FIG. 1C) DBT sulfone standard, (FIG. 1D) DBT standard;

FIG. 2 shows the far IR of DBT after reaction with; (FIG. 2A) Silica gel grade 22 at 180° C., (FIG. 2B) DBT after reaction with lab synthesized silica at pH 1, (FIG. 2C) DBT sulfone standard, (FIG. 2D) DBT standard. This graph shows the optimum temperature to oxidize DBT to DBT sulfone using silica grade 22 occurs at 160° C. in decalin. All the absorption bands are in the right place in the sample when compared to the standard. The peak on DBT at 744 cm$^{-1}$ has shifted in the sample to align up with the peak at 755 cm$^{-1}$ in DBT sulfone standard;

(FIG. 3A) DBT after silica lab synthesized dried at 380° C., (FIG. 3B) DBT after silica lab synthesized dried at 140° C. (FIG. 3C) DBT after silica lab synthesized dried at 100° C., (FIG. 3D) DBT sulfone standard, (FIG. 3E) DBT standard;

(FIG. 4A) DBT after silica lab synthesized dried at 380° C., (FIG. 4B) DBT after silica lab synthesized dried at 140° C., (FIG. 4C) DBT after silica lab synthesized dried at 100° C. (FIG. 4D) DBT sulfone standard, (FIG. 4E) DBT standard;

FIG. 7 is a x-ray diffraction pattern of: (FIG. 7A) silica grade 22 and (FIG. 7B) lab synthesized silica;

FIG. 8 shows the x-ray diffraction pattern and the peak indexing of DBT-sulfone standard (dotted line) and DBT after reaction with silica gel grade 22 (solid line)

DETAILED DESCRIPTION

Figure 1:
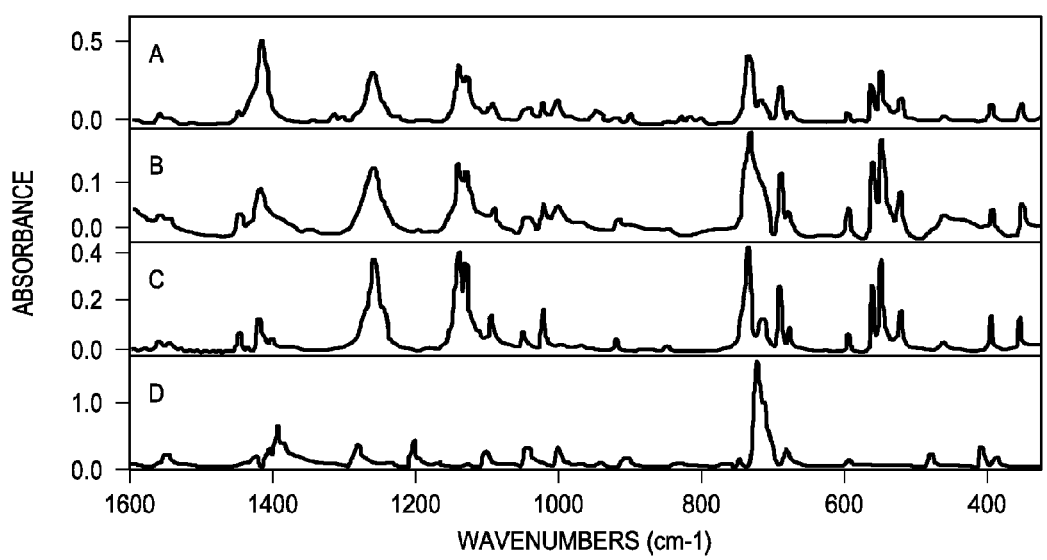
FIG. 1 shows the mid-IR of DBT after reaction with silica grade 22 and lab synthesized silica.

While the making and using of various embodiments of the present invention are discussed in detail below, it should be appreciated that, the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "hydrogen donor solvent" includes any organic or inorganic medium which is capable of transferring hydrogen to the hydrocarbon feedstock component under the present invention processing conditions.

The term "silica" as used herein embraces all finely divided, precipitated silicas which are produced by a wet process and, in addition, includes also pyrogenically obtained silicon dioxide. The term "silica gel" refers specifically to amorphous, regular density silica gel having a high surface area. More typically if is a coherent, rigid, continuous three-dimensional matrix or structure of generally spherical particles of silica having a pore volume of between about 0.5 and 3.5 cc/g and an average pore diameter of between about 80 and about 600 Angstroms. The term "amorphous silica" as used herein, refers to precipitated silica, or silica prepared by flame hydrolysis, which can also contain up to 20% aluminum oxide by weight. The filler content amounts to from 30 to 80% by weight. The term "ppm" is used to denote parts per million on an actives basis.

As used herein, the term "noble metals" Includes ruthenium, rhodium, palladium, osmium, iridium, gold and platinum. The term "acid catalysts" includes, in the broad sense, homogeneous mineral and organic catalysis, such as hydrochloric acid, sulphuric acid, acetic acid or para-toluenesulphonic acid, but also, and preferably, heterogeneous solid catalysts such as silica, alumina, silica-aluminas, zirconias, zeolites and acidic resins. The term "zeolite" as used herein refers to any porous natural or synthetic ceramic crystalline material that has a substantially uniform pore structure. The diameter of the pores of a zeolite generally range from about 2.5 to about 12 Angstroms. However, zeolites with a pore size of up to fen nanometers have been reported, (Science, Vol. 26, Mar. 25, 1994, pg. 1699). Most zeolites are metal oxides. The pore size of most zeolites is defined by the number of metal/oxygen atoms forming a ring or rings in the zeolite crystal structure.

The term "crude oil feed" as used herein relates to any full range crude oil from primary, secondary or tertiary recovery from conventional or offshore oil fields and feedstock's derived there from. "Crude oil feeds" may include any full range "syncrude" such as those can be derived from coal, shale oil, tar sands and bitumens. The crude may be virgin (straight run) or generated synthetically by blending. The term "asphaltene" as used herein refers to a material obtainable from crude oil and having an initial boiling point above 1200° F. (650° C.).

The present inventors recognized that silica-titania catalysts can be used for the mild oxidation of sulfur compounds, however, the reaction required the presence of hydrogen peroxide. Catalytic activity of $TiO_2$ has also been tested and reported that it will oxidize DBT in the presence of $H_2O_2$[26-27]. Furthermore, it has been reported that hydrogen can be oxidized to hydrogen peroxide using Au/SiO2 catalyst[34]. The presence of a hydrogen donor solvent is important, and it was also discussed how at a boiling temperature oxidation does not occur. This reaction may need the presence of both hydrogen and oxygen (which escapes at boiling temperatures) to produce in situ $H_2O_2$.

The present invention describes the use of acidic silica (pH 0-4) to oxidize dibenzothiophene (DBT) to dibenzothiophene sulfone in reflux conditions between 50° C. and 210° C. In the presence of a hydrogen donor solvent. In addition, the combination of silica with gold speeds up the oxidation process.

Oxidative desulfurization techniques generally use oxidizing agents such as $NO_2$, $H_2O_2$, and ter-butyl-hydroperoxide[9-12]. The advantage of using these techniques is that sulfur can be removed at relatively low temperatures and atmospheric pressure. The major drawback is that all of them require the use of an oxidizing agent. The constant use of strong oxidizing agents such as hydrogen peroxide can also become expensive and it makes these catalysts inadequate to be used in a large scale. Biodesulfurization mechanisms have also been tried since some bacteria are able to oxidize DBT at relatively low temperature and no pressure. In some cases, they bad starved organisms which need sulfur to survive, and then put them in a media were the only source of sulfur is DBT. Studies have shown that organisms would take sulfur out of DBT leaving behind the carbon rings. Some examples Pseudomonas putida CECT5277, genetically modified organism, which biodesifurates DBT[13]. Another type of bacteria are G. alkanivorans strain 1B was able to remove selectively the sulfur from DBT while keeping intact the remaining carbon-carbon structure[14]. Bacteria successfully oxidize dibenzothiophene (DBT) to dibenzothiophene-sulfone (DBT-sulfone) at low temperature, atmospheric pressure and without using an oxidizing agent; however, in order for these bacteria to survive, they need specific conditions such as specific pH and temperature which make them also inadequate technology to be taken a large scale in a refinery.

Bulk gold is well known as a chemically inert element to oxidation. Its chemical properties of gold have been attributed to the relativistic stabilization of the 6s level. Gold's chemistry is determined by the easy activation of the 5d electrons. It is also determined, as we know the electronic configuration of gold being [Xe] $4f^{14}$ $5d^{10}$ $6s^1$, by its desire to acquire a further electron to complete the $6s^2$ level and not to lose the one it has. However, chemical properties of bulk gold change in gold nanoparticles; recent studies have shown gold nanoparticles are catalytically active in the oxidation of CO[15].

In the present study, the oxidative catalytic properties of $AuSiO_2$ were investigated. Two types of support ($SiO_2$) were utilized. One was silica grade 22 commercially available and the other type was in-house lab synthesized silica. Silica gel was synthesized at different pH and tested in the model reaction. Infrared spectroscopy was used to follow the oxidation of DBT (dibenzothiophene) to DBT-sulfone using the in-house lab synthesized silica at the different pH. The oxidation reactions were also monitored at different reaction temperatures. X-ray diffraction was used to characterize the catalysts before and after the reactions. In addition, x-ray diffraction showed the conversion of DST to DBT sulfone. HPLC (High performance liquid chromatography) technique was used to determine the percentage removal of DBT.

Silica gel grade 22: Silica gel grade 22 was obtained from Alfa Aesar company (Ward Hill, Mass., USA). Oxidation properties of silica gel were tested using the model reaction. A solution using DBT and decahydronaphtalene (decalin) with a starting concentration of 2000 ppm of sulfur was prepared. Silica gel grade 22 was added to the solution, and the conversion of DBT to DBT-sulfone was tested at six different temperatures. The temperatures tested were 50° C., 100° C., 120° C., 140° C., 180° C. and boiling temperature (190° C. to 210° C.). Different temperatures were tested to determine the optimum temperature at which oxidation would occur. The duration of each reaction was 4 h. In order to determine if the oxidation reaction depended only on the temperature, solvent or both, different types of solvents were used hydrogen and non-hydrogen donor with different boiling temperatures. The used solvents were decahydronaphtalene (decalin), tetrahydronaphtalene (tetralin), heptane, dodecane, and toluene as solvents.

Synthesis of silica gel at different pH: Silica gel was prepared with slight modifications as previously reported[15]. Sodium metasilicate ($Na_2SiO_3$) and hydrochloric acid (HCl) were obtained from Alfa Aesar. $Na_2SiO_3$ was dissolved in water which gave a basic solution (pH 12-14). HCl was added to the solution under vigorously stirring to bring the pH down to 10. The solution looked cloudy because precipitation started to occur. The gel was then washed several times with water to remove any NaCl and then washed with alcohol to remove any water. The gel was then dried at three different temperatures 100° C. (24 h); 140° C. (24 h) and 380° C. (24 h). The same procedure was followed to synthesize $SiO_2$ at pH 9 and 8. As the pH was getting closer to neutral, more precipitation was observed. At pH 7 $SiO_2$ gel Instantly precipitated out and the same procedure as previously described was followed. To synthesize $SiO_2$ gel at pH 6, 5, and 4, two different methods were used. One method consisted in doing the titration with HCl fast to avoid passing through the gel phase at pH 7. The other method consisted in bringing the pH down to about 2, after that it was brought up with sodium hydroxide (NaOH) to pH 6, 5, and 4.

Finally, $SiO_2$ was synthesized at acidic pH, HCl was added to the solution of $Na_2SiO_3$ in water under vigorously stirring and very fast to reach a pH of 0. The solution went from clear to yellow. Then, the solution was heated at a 100°

C. to obtain a gel. The gel was washed with water and alcohol and dried at the three different temperatures. The oxidative properties of $SiO_2$ synthesized at different pH were tested using the model reaction. DBT (0.5 g) was dissolved in decalin (50 ml), 0.5 g of $SiO_2$ was added and let the reaction stir for 4 h. The reactions were tested at 6 different temperatures: 50° C., 100° C., 120° C., 140° C., 180° C. and boiling temperature of the solvent. Different temperatures were tested to determine the optimum temperature for the oxidation reaction to occur. Also, different solvents were tested: decalin, tetralin, toluene, heptane, and dodecane solvents were tested in the reaction. The use of different solvents was use to determine if the solvent or the temperature or both were important factors in the oxidation reaction of DBT to DBT-sulfone.

Synthesis of gold nanoparticles on silica: Silica was dispersed in water. A 3 mM solution of gold was prepared by dissolving $HAuCl_4$ (sold tetrachloroaurate) in water. The gold solution was then added to the dispersed silica. Reduction of gold on the silica was accomplished using $NaBH_4$. Gold was reduced from $Au^{3+}$ to $Au^0$. The nanoparticles were then washed several times with distilled wafer and centrifuged to wash out salts from the precursors. Then, they were oven dried at: a temperature of 100° C.

X-ray diffraction analysis (XRD): The x-ray diffraction data was collected using a D5000 X-ray diffractometer with Cu-Kα radiation which its wavelength corresponds to 1.540562. The start angle was 5 degrees and the stop angle was 45 degrees. This range is where DBT and DBT sulfone diffract that is why it was chosen. The electron flux was 10 kEv. The slits used where 0.1 and 1.0, X-ray analyses were performed on the silica before running the reaction. X-ray diffraction was used to characterize the size of the gold nanoparticles before and after the reaction with DBT. After the reaction, the solutions of DBT, solvent, catalyst and conversion products were left to evaporate. After the solvent is gone, all the silica concentrates on the bottom of the big watch glass. If was then easy to remove the silica. Then the solid left behind was mixed in a homogenous mixture and a representative sample was taken and analyzed using x-ray diffraction.

X-ray diffraction was also performed on the silica, removed to investigate any changes occurred in the silica structure. In addition, after the mixture of DBT and DBT-sulfone obtained was analyzed, unconverted DBT was extracted using decalin a non-polar solvent to calculate the mass balance ratio of DBT to DBT-sulfone. DBT sulfone is completely insoluble in decalin and the other non-polar solvents used in the different reactions. DBT-sulfone showed solubility in ethanol and acetone. However, acetone was not used to do the extractions because DBT is also soluble in acetone.

FT-IR Data collection: Infrared studies were carried out with a Bruker FTIR-IFS 66 v. The samples for IR measurements were prepared as pellets by embedding the sample in a polycrystalline KBr matrix. The pressure applied to make the pellets was 5 MPa. A background collection was run before each sample collection. After being treated with the catalysts, the solutions of the different solvents, DBT, and the catalyst were left in the hood to slowly evaporate the solvent. The evaporation was performed in big watch glasses. After the solvent is gone, all the silica concentrates on the bottom of the big watch glass. The silica was then removed. Then the solid left behind was mixed in a homogenous mixture and a representative sample was taken and analyzed using infrared spectroscopy. DBT and DBT sulfone standards were mixed in different percentages to compare them to the samples and determine the percentage of DBT and DBT sulfone.

In addition, after the mixture of DBT and DBT-sulfone obtained was analyzed, DBT was extracted using decalin. DBT sulfone is completely insoluble in decalin and the other non-polar solvents used. After the extraction was performed, the mass balance was calculated and it confirmed the data obtained from the infrared spectroscopy analysis. When the reactions were run in the temperature range of 100° C. to 140° C., it was not possible to separate completely DBT-sulfone from the silica not even using a non-polar solvent.

High Performance Liquid Chromatography (HPLC): High Performance Liquid Chromatography was used to determine the percentage of DBT removed. High Performance Liquid Chromatography (HPLC) was performed with a SPHERI-5 (5 micron) Silica Based column, a Spectra-Physics Spectra System P1500 gradient pump, UV2000 defector, and Winner for Windows Software. The mobile phase normally used was 95% hexanes, 5% isopropanol by volume with helium solvent de-gassing. The flow rate was set to 1 mL/min. and the detector was set to a 256 nm wavelength, all at room temperature. A 1 μl aliquot of analyte was used, in some samples the injection amount was higher to enhance the signal since it appeared, too weak. A calibration curve was obtained by using four different concentrations of DBT. The R factor of the calibration curve was 99%. Then using the line equation y=mx, y corresponded to the counts, m to the slope of the curve and x was calculated to determine the concentration of DBT that was removed, in order to determine the role of gold on the silica, the concentration of DBT was followed at three different times using just $SiO_2$ and $AuSiO_2$.

XRD Results: X-ray diffraction patterns of DBT after treated with the $AuSiO_2$ and DBT-sulfone standard are shown in FIG. 8. Cerius software was used to assign the h k l planes, DBT-sulfone was modeled using the cell parameters and atomic positions as previously reported[17]. The unit cell parameters used were a=10.09 Å, b=13.89 Å, c=7.22 Å and β=93.5°. The space group used was C2/c. The x-ray diffraction patterns showed a difference in intensities (FIG. 8). Reflections at 13.30 and 22.14 2 theta that correspond to the planes 020, and 220 are the same intensity in DBT-sulfone standard and DBT after treated with silica gel. However, reflections at 11.28, 16.86, 17.20, 18.32, 25.88, 27.51, and 38.32 2theta corresponding to 110, −111, 021, 040, 221, 041 and −113 planes are a lot higher than in the treated sample. Usually, intensify in x-ray diffraction is concentration related. Yet, the ratio of the intensities between the two reflections at 11.28 and 16.6 2 theta, which are the main peaks in DBT-sulfone standard, is 5.31. The ratio of the intensities in the treated sample between the peaks at 11.28 and 16.69 2 theta is 0.78. In addition, the ratio of intensities of 11.24 to 16.88 is 0.73 in the treated sample whereas in the DBT-sulfone standard is 0.52. Since the ratio of the intensify of the peaks is different between DBT-sulfone standard and the sample treated, the difference in Intensity is not concentration dependent. The treated sample may have adopted preferred Orientation in the 110, −111, 021, 040, 221, 041 and −113 planes since they are the predominant peaks. It is possible the height peaks are different just because the treated sample was more crystalline than the purchased sulfone. The way the treated sample was extracted from the solvent was by slow evaporation which led to the formation of DBT-sulfone crystals.

Only when the reaction was run at higher temperatures between 160° C. and 180° C., DBT-sulfone crystals could be extracted and observed in the x-ray diffraction Pattern. When the reaction was run at a lower temperature between 50° C. and 140° C. DBT-sulfone could not be completely isolated and the x-ray diffraction pattern showed silica and DBTsulfone peaks. Even though silica gel is amorphous it does have a broad peak at about 20° 2theta. In this region DBT-sulfone has many reflections that could not be observed when the reactions were run at lower temperature.

Reactions using the in-house lab synthesized silica were also run at different temperatures. However, the best percent removal of DBT, as occurred in the case of silica gel grade 22, was obtained when the reactions were run at 160° C. In addition, silica gel grade 22 and the acidified silica synthesized and dried at 380° C. were characterized using also x-ray diffraction (FIG. 7A and FIG. 7B). X-ray diffraction of in-house lab synthesized silica dried at 100° C. and 140° C. are not shown but the x-ray diffraction pattern doesn't differ from the one belonging to the in-house lab synthesized silica dried at 380° C. After reaction, both samples were analyzed again using x-ray diffraction. They looked still the same as before reaction, as amorphous silica (data not shown).

FT-IR Results: The results of the reaction using DBT as the model compound are shown in FIGS. 1A-1D. These results correspond to the reactions carried at 160° C. using silica grade 22 and the lab synthesized silica (pH 2-0) as catalysts (FIGS. 1A and 1B). This sample had an Initial concentration of 2,000 ppm of sulfur. The solvent used was decalin, FIG. 1C and FIG. 1D show the infrared spectrum corresponding to DBT-sulfone standard and DBT respectively. The main differences that were observed when the reaction is run at different temperatures are in the range of 1000 to 1500 $cm^{-1}$. The absorption bands corresponding to DBT-sulfone start appearing when the reaction is ran at 100° C. (data not shown). This absorption bands appear in the range from 500 to 800 $cm^{-1}$ belonging to SO vibrations are present. However, DBT-sulfone vibrations between 1000 $cm^{-1}$ and 1500 $cm^{-1}$ are not visible because they are being masked by the presence of the silica, which absorbs in the range of 1000 and 1500 cm–1 (data not shown). As the reaction is run at higher temperatures, the absorption bands of DBT-sulfone standard in the range of 1000 to 1500 $cm^{-1}$, start becoming visible in the samples treated with the catalyst. Based on this data, it is suggested that at lower temperatures, DBT is adsorbed onto the silica and oxidized. As the temperature at which the reaction is run Increases (160° C.-180° C.), the silica releases the DBT already oxidized as DBT-sulfone back to the solution as shown in FIG. 1A all the vibrations present in the spectrum correspond to DBT-sulfone.

Figure 2:
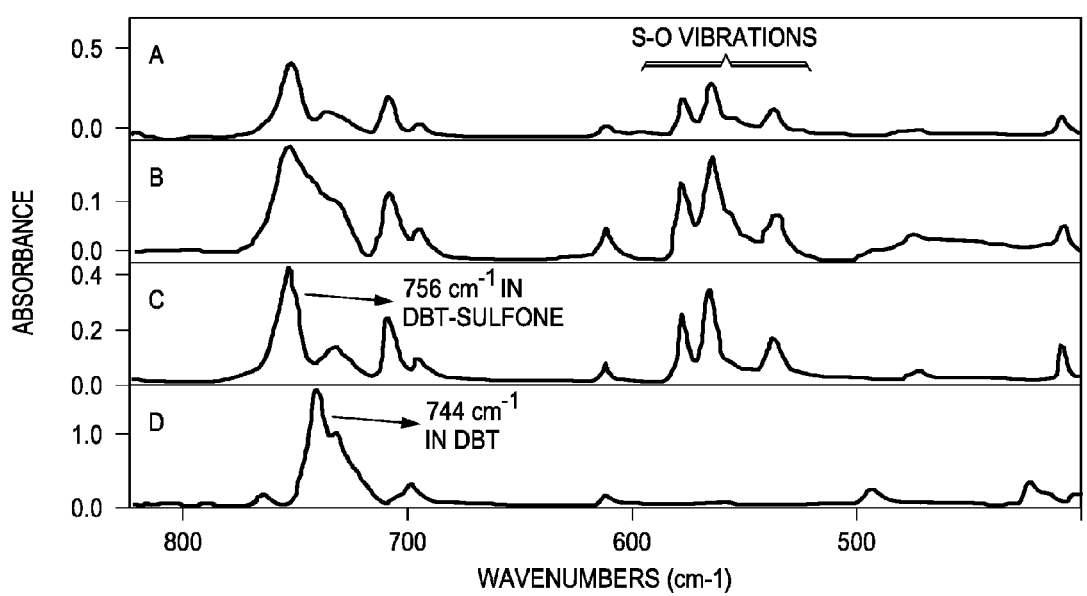

In FIGS. 2A-2D, the infrared spectrum is shown only from 800 to 400 $cm^{-1}$ wavenumbers because it is where the C—S and S—O ring vibrations occur. It is important to emphasize the difference in the infrared spectrum after the catalyst treatment at 160° C. (FIG. 2A). The shift in the peak at 744 $cm^{-1}$ occurs in the treated sample and the absorption bands corresponding to S—O vibrations appear in the 600-500 $cm^{-1}$ range (FIG. 2A). FIG. 2B shows the far IR of DBT after reaction with lab synthesized silica at pH 1.0. Comparing the treated sample to DBT standard (FIG. 2D) there is no visible DBT vibrations.

Comparing the treated sample to DBT sulfone standard (FIG. 2C), all the vibrations of the DBT sulfone standard are present in the treated sample. Based on the aforementioned results, it was determined the range temperature, at which the oxidation of DBT to DBT-sulfone occurs, is between 100° C. end 180° C. in decalin. Yet, in order to obtain the sulfone detached from the silica, the reaction needs to be carried at higher temperature (160° C.-180° C.).

The main differences that were observed when the reaction is run at different temperatures are in the range of 1000-1500 $cm^{-1}$. The absorption bands corresponding to DBT-sulfone start appearing when the reaction is run at 100° C. (data not shown). However, DBT-sulfone vibrations between 1000 $cm^{-1}$ and 1500 $cm^{-1}$ are masked by the presence of the silica, which absorbs in the range of 1000-1500 $cm^{-1}$ and thus not visible in the FT-IR spectra. As the reaction temperature increased: the absorption bands of DBT-sulfone standard in the range of 1000-1500 $cm^{-1}$, began to become visible in the samples treated with $SiO_2$. Based on these data, it is suggested that a lower temperature DBT is absorbed onto the silica first and is subsequently oxidized. As the temperature at which the reaction is run increases (160° C.), the silica releases the oxidized DBT (DBT-sulfone) back to the solution. The reaction was also carried at boiling temperature of the decalin (190° C.). At boiling temperature, oxidation did not occur, not even partial oxidation. The analyses at boiling temperature showed no decrease of concentration of DBT, or the presence of DBT-sulfone. Therefore, the temperature range at which reactions are carried is an important factor in the oxidation of DBT.

Figure 3:
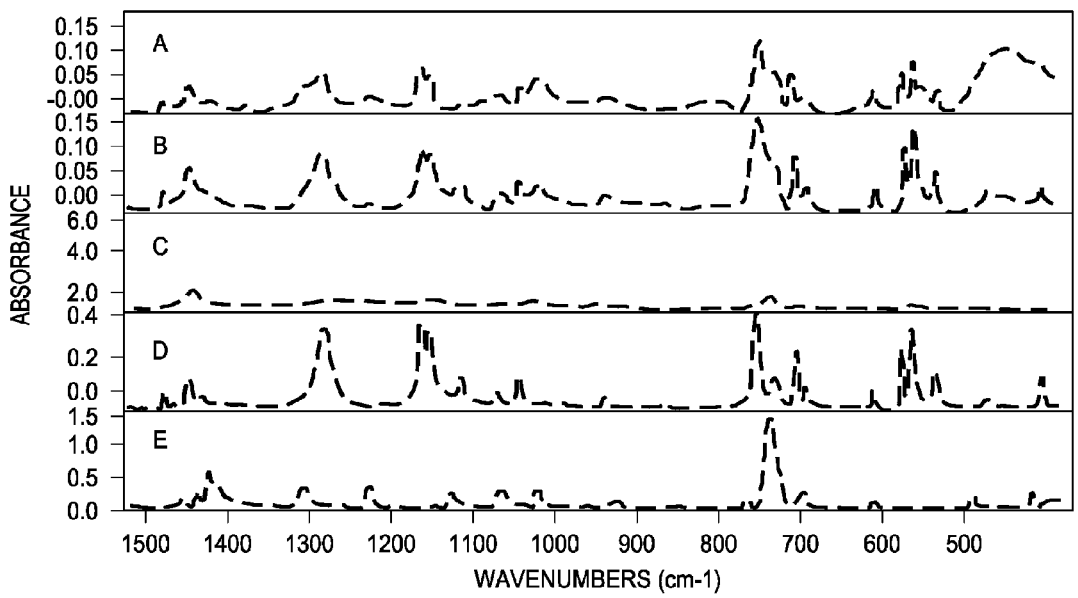
FIG. 3 shows the DBT after reaction with lab synthesized silica. The different spectra correspond to the silica dried at different temperatures.
Figure 4:
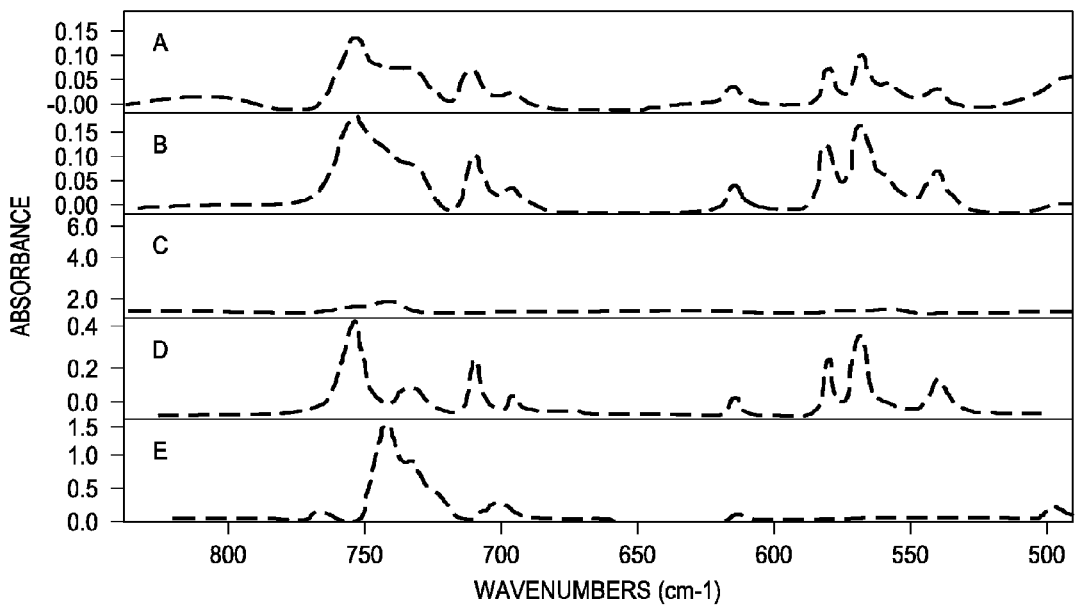
FIG. 4 shows the far-IR of DBT after reacted with lab synthesized silica and dried at different temperatures.

FIGS. 3A-3E is showing the infrared spectra corresponding to DBT after the reaction with lab synthesized silica. The reaction was carried at 160° C., FIGS. 3A-3C shows DBT after reaction with lab synthesized silica dried at different temperatures 100° C., 140° C. and 380° C. FIGS. 3A and 3B show DBT after reaction with lab synthesized silica dried at 140° C. and 380° C. respectively. FIG. 3C shows DBT after reaction with lab synthesized silica dried at 100° C. Absorption bands of FIGS. 3A and 3B coincide with the absorption bands in FIG. 3D (DBT-sulfone standard, FIG. 3E); however, when the lab synthesized silica is dried at 100° C., conversion of DBT to DBT sulfone is not as evident. FIGS. 4A-4E shows the far IR, FIGS. 4A and 4B show all the absorption bands corresponding to DBT sulfone. The shoulder at 734 $cm^{-1}$ present in DBT-sulfone is broader in the treated samples with lab synthesized silica (FIGS. 4A and 4B). The broadening of the peak could be due to the presence of decalin (solvent where the reaction was carried) which absorbs at this same wavenumber. FIG. 4C shows the far-IR of DST after reacted with lab synthesized silica dried at 100° C. FIGS. 4D and 4E shows the far-IR of DBT sulfone and DBT standard, respectively.

Figure 5A:
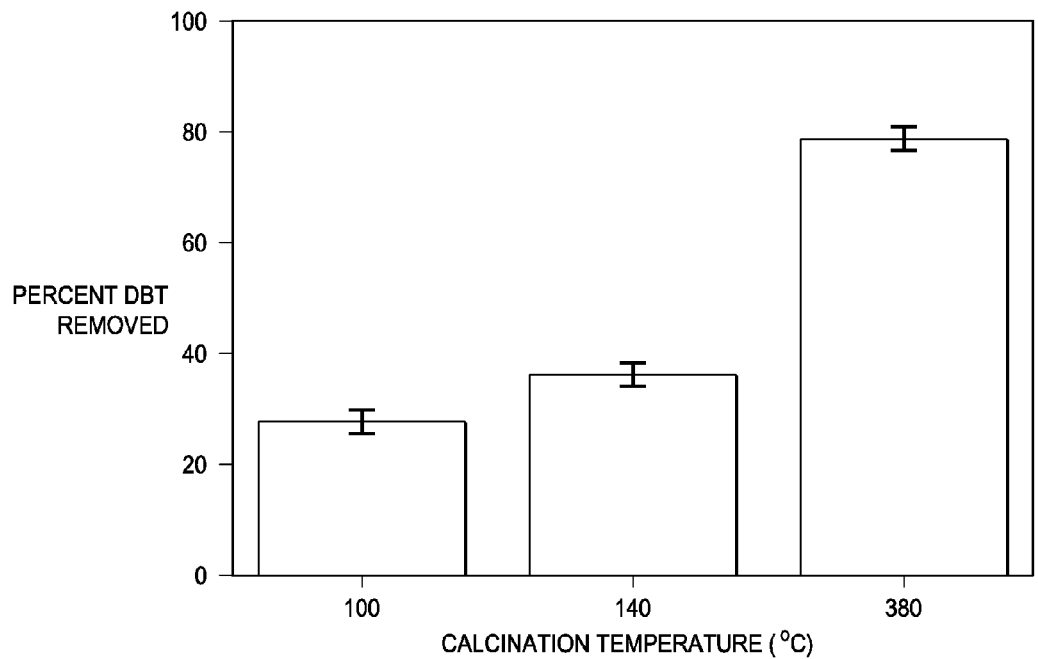
FIG. 5A is a graph that shows different drying temperatures of the in-house lab synthesized silica in function of % of DBT removed.
Figure 5B:
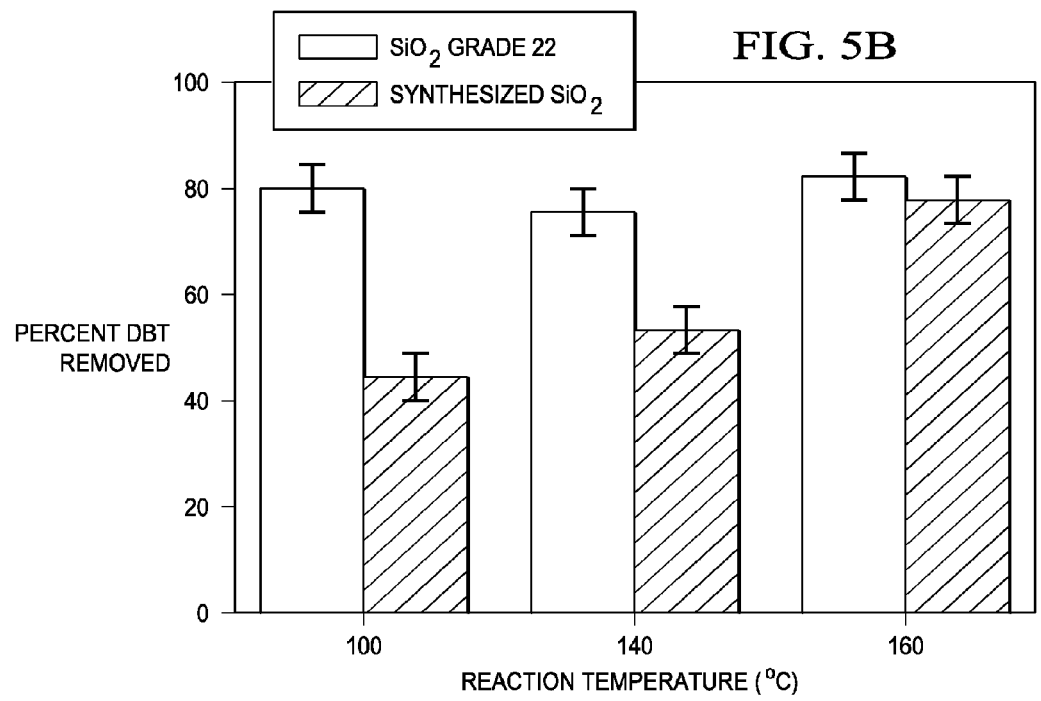
FIG. 5B is a graph showing the effect of reaction temperature on the removal of DBT in the presence of $SiO_2$ grade 22 and synthesized acidic $SiO_2$ calcinated at 380° C.
Figure 5C:
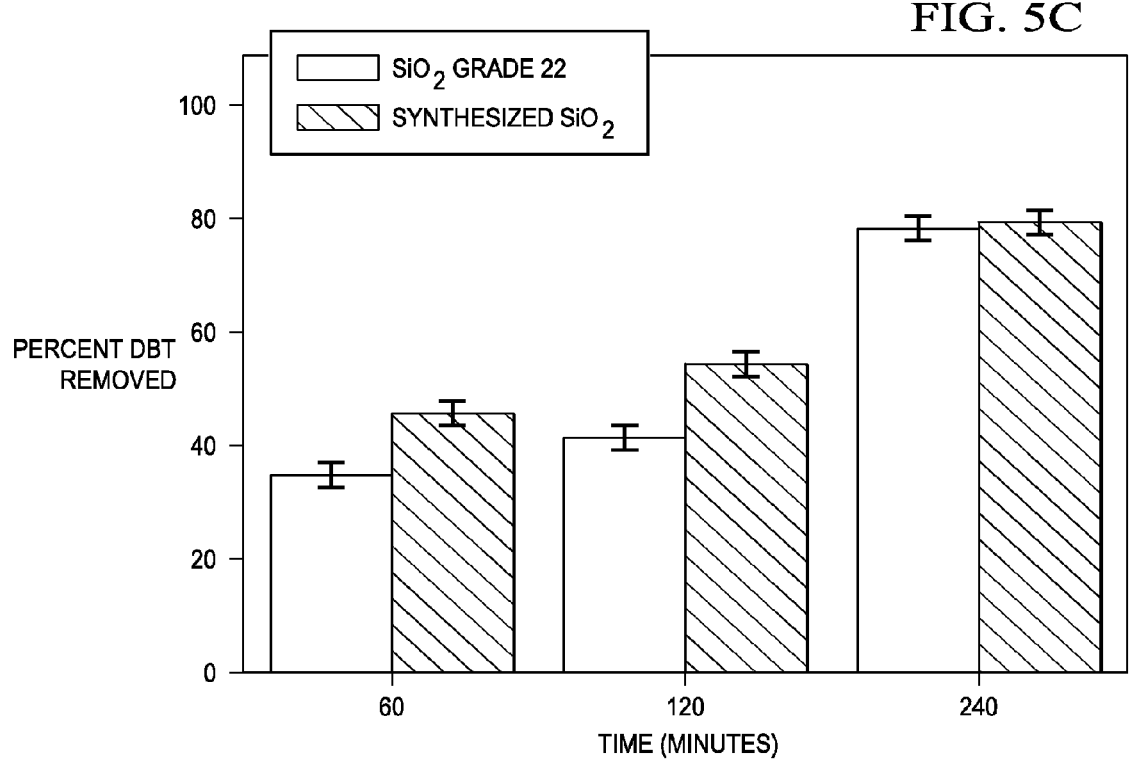
FIG. 5C is a graph showing the comparison of time of the removal of DBT using $SiO_2$ grade 22 and synthesized acidic $SiO_2$ (calcinated at 380° C.) at a reaction temperature of 160° C.
Figure 6:
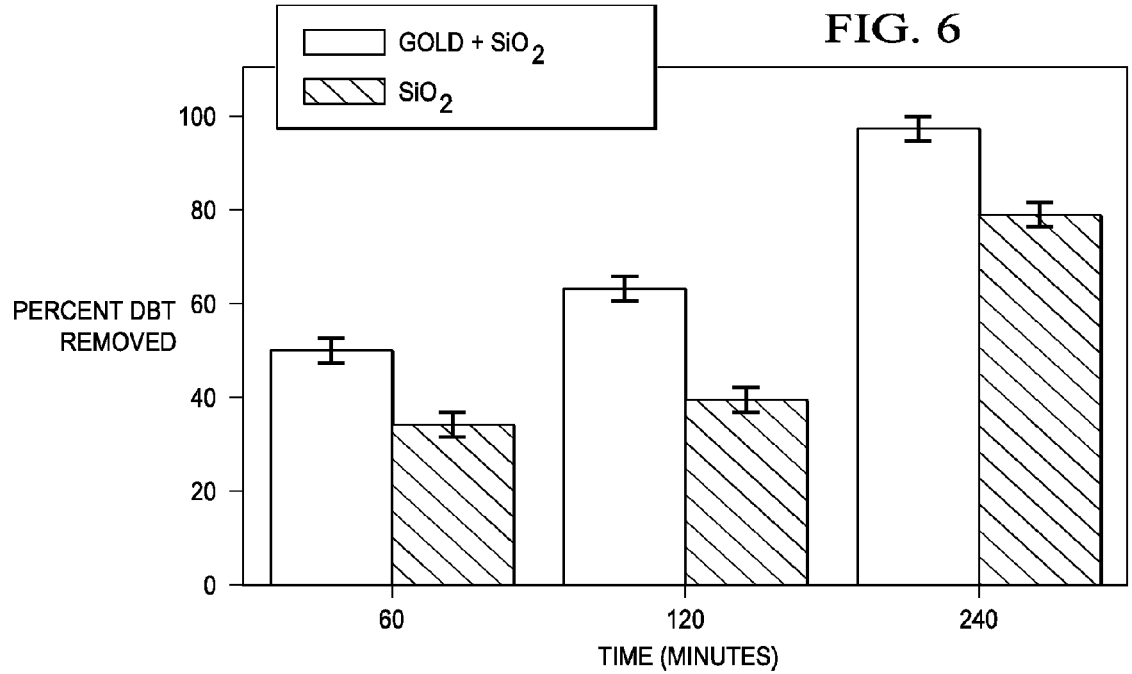
FIG. 6 is a graph that shows the % of DBT removed in function of time. The % of DBT removed is shown in white when $AuSiO_2$ is used and when only $SiO_2$ the % of DBT removed is shown in red.

HPLC Results: HPLC technique was used to confirm the percentage conversion of DBT to DBT-sulfone obtained from IR and mass balance analysis. The retention time for DBT was 4.2 minutes. The starting concentration of DBT was 2,000 ppm of S. FIG. 5A shows the % of DBT removed in function of the drying temperature of the lab synthesized silica. It can be observed that as the drying temperature increases, the % of DBT removed increases too. As it can be seen in FIG. 5A when the gel is dried at 100° C. only a 20% reduction of the DBT concentration was observed. The concentration of DBT removed when the $SiO_2$ was calcinated at 140° C. was 40%. However, at a calcination temperature of 380° C. (above the critical point of water), a reduction of 80% of the DBT concentration was observed. Thus, the drying temperature that gave out the best % of DBT removal was 380° C. It is possible that this result was obtained because it has been reported that drying silica at 380° C. (above the critical point of water) yields a material with high surface area. The present inventors performed a comparison between commercially available silica and the in-house-synthesized silica for the oxidation of DBT was performed. The reactions of both the in-house-synthesized silica and the commercial silica with DBT were performed at 100° C., 140° C., and 160° C. and are shown in FIG. 5B. From the three temperatures used 100° C., 140° C. and 160° C., the reaction run at 160° C. was the one that showed the largest removal of DBT. Furthermore, as shown in Table 1, that the oxidation of DBT to DBT-sulfone occurs only in the presence of a hydrogen-donating solvent such as decalin or tetralin. No oxidation was observed when non-hydrogen donor solvents such as heptane and toluene were used. The conversion using either tetralin or decalin is approximately the same. Only data using decalin as a solvent are shown in FIG. 5B. According to FIG. 5B, the highest removal, 85%, of DBT occurred at 160° C. FIG. 5C shows the time requirements for the removal of DBT at 160° C., using sampling times of 60, 120, and 240 min. The reaction requires 240 min to reach 80-85% removal of DBT.

TABLE 1

Results of reactions of DBT with different $SiO_2$: commercially available $SiO_2$ grade 22, $SiO_2$ basic, $SiO_2$ neutral, and $SiO_2$ acid in house synthesis, using different solvents, and reaction temperatures.

| Catalyst | Reaction temperature (° C.) | Solvent | % DBT removal |
|---|---|---|---|
| $SiO_2$ grade 22 | 160 | Decalin | 80 |
| $SiO_2$ grade 22 | 160 | Tetralin | 85 |
| $SiO_2$ grade 22 | 100 | Heptane | 0 |
| $SiO_2$ grade 22 | 110 | Toluene | 0 |
| $SiO_2$ grade 22 | 160 | Dodecane | 0 |
| $SiO_2$ neutral pH | 160 | Decalin | 0 |
| $SiO_2$ basic pH | 160 | Decalin | 0 |
| $SiO_2$ acidic pH | 160 | Decalin | 80 |
| $SiO_2$ neutral pH | 160 | Tetralin | 0 |
| $SiO_2$ basic pH | 160 | Tetralin | 0 |
| $SiO_2$ acidic pH | 160 | Tetralin | 84 |

FIG. 8 shows the % of DBT removed in function of time using $SiO_2$ and $AuSiO_2$. It can be observed that using gold nanoparticles increases the % of DBT removed at a given time. Table 2 shows a summary of the results of the reactions run using silica and the different solvents. As it was shown previously, temperature influences the oxidation of DBT but also the reaction is solvent depended. Decalin is a well known hydrogen donor molecule which boils at 190° C. The oxidation reaction was also carried in tetralin (1,2,3,4 tetrahydronaphtalene) at the same temperatures the decalin reaction was carried, 100° C., 120° C., 160° C., 195° C. and boiling temperature. The boiling temperature of tetralin is 205° C., The reactions carried in tetralin had the same behavior the reactions carried in decalin had. At lower temperatures, the DBT-sulfone was stuck on the silica and at higher temperatures was released back to the solution. At the boiling temperature of tetralin and decalin, oxidation didn't occur. As temperature increases, gas solubility decreases as if is known from Henry's Law. It is possible at boiling temperature the solvents degas and there is no more oxygen available to oxidize DBT. Non-hydrogen donor molecules were also used as solvents. The reactions were carried in heptane, dodecane and toluene at different temperatures. Oxidation of DBT didn't occur in any of these solvents at any temperature. It was concluded a hydrogen donor solvent was necessary to oxidize DBT.

TABLE 2

List of different reactions carried out and the percent conversion from DBT to DBT-sulfone.

| Catalyst | Temperature Reaction | Solvent used in reaction | % conversion of DBT to DBT-sulfone |
|---|---|---|---|
| Silica lab synthesized neutral pH | 160° C. | Decalin | 0% |
| Silica lab synthesized at basic pH | 160° C. | Decalin | 0% |
| Silica lab synthesized at acidic pH (0-2) | 160° C. | Decalin | 80.4% |
| Silica lab synthesized neutral pH | 160° C. | Tetralin | 0% |
| Silica lab synthesized at pH basic pH | 160° C. | Tetralin | 0% |
| Silica lab synthesized at acidic pH (0-2) | 160° C. | Tetralin | 85.3% |
| $AuSiO_2$ | 160° C. | Decalin | 90.5% |
| $AuSiO_2$ | 160° C. | Tetralin | 92.4% |

Table 1 shows a summary of the results of the reactions run using silica and different solvents. As can be seen in Table 1, both the reaction temperature and solvent directly affect the oxidation of DBT to DBT-sulfone. The oxidation reaction was also carried out in tetralin (1,2,3,4 tetrahydronaphthalene, data shown in Table 2) at the same temperatures at which the decalin reaction was carried out, 100° C., 120° C., and 160° C., The reactions carried out in tetralin had the same behavior as the reactions carried out in decalin. At lower temperatures, the DBT-sulfone was stuck on the silica and at higher temperatures was released back to the solution. At the boiling temperature of tetralin and decalin, oxidation did not occur. This suggests that dissolved gases (such as $O_2$) in the solvent may be partially responsible for the oxidation; as the temperature Increases the solubility of the gases decreases. At the boiling point of the solvent ail the dissolved gases are released and thus there is no gas left in the solution for the conversion of DBT to DBT-sulfone. In addition, the reactions were also studied in non-hydrogen-donating solvents; heptane, dodecane, and toluene at different temperatures. The oxidation of DBT to DBT-sulfone did not occur in either of these solvents at any tested temperature. These findings suggest that in addition to needing a dissolved gas in the solvent a hydrogen-donating molecule is also necessary to oxidize DBT.

In addition to temperature and solvent, the pH at which silica gel was synthesized had a role in the oxidation reaction. Silica gel synthesized in the pH range of 3-10 did not oxidize DBT. Oxidation of DBT only occurred when silica synthesized at pH in the range of 1-2 was used. The structure of the silica is depending upon what pH the silica gel is synthesized. An acidic pH silica gel will have H+ embedded in the matrix or OH- at a basic pH[18]. Under acidic conditions condensation occurs mainly between neutral silanol groups (Si—OH) and protonated silanol groups (Si—OH+) located at the monomers and at the ends of polymeric chains leading to the formation of linear polymers[19]. In basic conditions, condensation occurs by attack of a deprotonated silanol (Si—O-) located at the middle of chains, to a neutral silanol (Si—OH) or Si—OR group which are at the ends of chains. The aggregation processes are different for pH=2 and for pH≥6[19]. In the former case there is cluster-cluster aggregation, and in the latter case there is reaction limited monomer-cluster aggregation. In this way, for basic conditions, slioxane bonds are broken producing monomers that are not hydrolized. Comparatively, the acid-catalyzed or acidic $SiO_2$ compounds contain higher concentrations of adsorbed water, silanol groups, and unreacted alkoxy (depending on the source of the Si in the synthesis) groups than base-catalyzed precipitates[18]. From the results in the present invention the oxidation of DBT occurs only in the presence of acidic silica, which suggests that the SiOH+ groups are important in the reaction mechanism. For neutral conditions, the hydrolysis rate is low leading to the presence of monomers that are partially or non-hydrolyzed at all[20-21]. Thus, under neutral and basic conditions a large concentration of monomers remains. These monomers wilt condense preferentially with clusters as the condensation process occurs preferentially between deprotonated silanol species and neutral silanol species[20-21]. Acid-catalyzed silica gels contain higher concentrations of adsorbed water, silanol groups, and unreacted alkoxy groups than did the base-catalyzed precipitates[22]. Therefore, the fact that oxidation of DBT occurs only when silica gel is synthesized at an acidic pH, it is hypothesized, $H^+$ protons are necessary to drive the oxidation reaction.

It has been reported that sulfides can be oxidize to sulfoxides using supported $HNO_3$ on silica gel and polyvinylpyrrolidone (PVP) in the presence of a catalytic amt of KBr or NaBr[23]. Oxidation using silica gel may be an acid catalyzed reaction since the silica has to be acidic and the solvent a hydrogen donor[24-25]. Drying temperature of the silica gel synthesized did have an impact in the oxidation reaction. Silica gel dried at 160° C., had the best percentage conversion of DBT to DBT sulfone. It was also the one that according to the data obtained from the x-ray diffraction pattern, had a similar structure to silica grade 22. Drying temperatures usually lead to structural changes. High temperature drying usually yields a crystalline structure. The temperatures used to dry the synthesized silica were not high enough to yield a crystalline structure. If the drying temperature of silica had been higher the structure of the silica would had been affected. This assumption is made on the fact that quartz, which is a crystalline phase of silica, was tested in the oxidation reaction. No conversion of DBT to DBT sulfone was observed.

There are no DBT oxidation reactions reported in literature which would require the presence of a hydrogen donor solvent. The literature reports the use of peroxides when oxidizing DBT and the use of oxidizing solvents such as aldehydes and carboxylic acid[26-27]. For example, it has been reported the use of a surfactant-type decatungstates for the oxidation of DBT. This reaction requires hydrogen peroxide[28]. Also, oxidative desulfurization of dibenzothiophene catalyzed by Keggin-type $H_3PMo_{12}O_{40}$ and $Na_3PMo_{12}O_4$ using hydrogen peroxide as the oxidizing agent is found in the literature[29]. It has been reported the use of silica-titania catalysts for the mild oxidation of sulfur compounds but the presence of hydrogen peroxide is needed. Catalytic activity of $TiO_2$ has also been tested and reported that it will oxidize DBT in the presence of $H_2O_2$[30-31]. As already mentioned, there is plenty of evidence $H_2O_2$ will oxidize DBT to DBT sulfone[32-33] therefore, it is also hypothesized the in-situ production of $H_2O_2$ by silica. It has been reported that hydrogen can be oxidized to hydrogen peroxide using $Au/SiO_2$ catalyst[34]. The presence of a hydrogen donor solvent is important, and at a boiling temperature oxidation does not occur. This reaction may need the presence of both hydrogen and oxygen (which escapes at boiling temperatures) to produce in situ $H_2O_2$.

Figure 9:
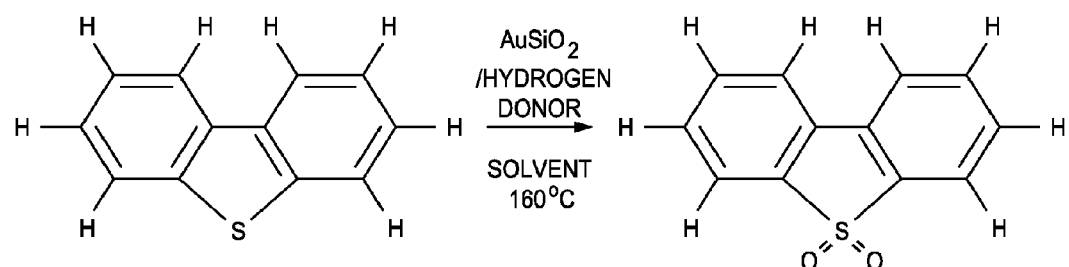
FIG. 9 shows oxidation of DBT to DBT-sulfone using $AuSiO_2$, a hydrogen donor solvent at a temperature of 160° C.

Amorphous acidified silica (synthesized at an acidic pH) gel will oxidize DBT to DBT sulfone in the presence of a hydrogen donor solvent in the temperature range of 50° C. to 210° C. depending on the boiling point of the hydrogen donor solvent. The current study addresses the use of acidified silica gel for the oxidative desulfurization of DBT in the presence of a hydrogen donor solvent, at relatively low temperature and atmospheric pressure, with no oxidizing agent present in the reaction (FIG. 9). DBT has been used as a model compound of the sulfur containing compounds present in heavy feeds. This model has been successful in predicting the behavior of catalysts in the real feeds. According to the results obtained, sulfur compounds in heavy feeds, could be oxidized and removed with a polar solvent such as ethanol. Following the results obtained from the model reaction it is concluded that using acidified silica is an inexpensive and efficient way to upgrade heavy feeds.

Process to extract the DBT-sulfone: After the reactions were run, the solution of decalin and products can be mixed with 50 mL of ethanol. Using a separating funnel, the two phases can were separated. The DBT-sulfone migrated to the ethanol due to the change in polarity in the molecule. The addition of the two oxygen atoms to the DBT, made the DBT-sulfone completely insoluble in decalin. Once the two phases were separated, the solvents were removed using a roto-evaporator.

Asphaltene reduction: In addition, to testing the catalysts in the DBT-model reaction, the present inventors also tested them in real crude oil. The crude oil used contained 10% wt asphaltene. By definition, asphaltene is any fraction of the crude oil insoluble in heptane solvent. The control reaction was run by refluxing 18 g of the crude oil in 30 ml of heptane for 4 h at 98° C. The solution was then filtered to obtain 1.8 g of the solid filtrated which corresponded to 10% asphaltene of the crude oil. Two separate reactions were also run using silica-gold nanoparticles, and iron-gold nanoparticles in crude oil (18 g). The solvent used was heptanes, the reflux temperature was 98° C. and the duration of the reactions was 4 h. The solutions were then filtrated and the solids corresponded to 0.7 g and 1.44 g for silica-gold and iron-gold nanoparticles respectively. Therefore, the gold nanoparticles on silica can be used to reduce the number of asphaltene in crude oil because the results show a decrease of 10% to 4%.

The present invention Includes the use of acidic silica (pH 0-4) to oxidize dibenzothiophene (DBT) to dibenzothiophene sulfone in reflux conditions between 50° C. and 210° C. In the presence of a hydrogen donor solvent. The catalysts were characterized using x-ray diffraction (XRD), infrared spectroscopy and x-ray fluorescence (XRF). Infrared spectroscopy was also used to follow the oxidation of DBT to DBT sulfone.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and Individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly Included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,713,408: Process for the catalytic hydrotreating of silicon containing hydrocarbon feed stock.
U.S. Pat. No. 4,329,221: Upgrading of hydrocarbon feedstock.
United States Patent Application No. 20100038287: Process for removing silicon compounds from hydrocarbon streams.

1) Venkateshwar Rao T., Sain B., Kafola S., Ram Nautiyal B., Kumar Sharma Y., Madhusudan Nanoti S., Omkarnath Garg M. Oxidative Desulfurization of HDS Diesel Using the Aldheyde/Molecular Oxygen Oxidation System. Energy & Fuels 200 (2007) 3420-3424.
2) Chianelli R. R., Daage M., Structure-Function Relations in Molybdenum Sulfide Catalysts: The "Rim-Edge" Model, Journal of Catalysis 149 (1994) 414-427.
3) Babich I. V., Moulijn J. A., J.A. Science and Technology of novel processes for deep desulfurization of oil refinery streams; a review. Fuel 82 (2003) 607-631.
4) Song, O, Ma. X., New design approaches to ultra-clean diesel fuels by deep desulfurization and deep dearomatization. Applied Catalysis 8: Environmental 41 (2003) 207-238.
5) Sampanthar T. J., Xiao H., Dou J., Nahn T. Y. Rong X., Kwan Pui W., A novel oxidative desulfurization process to remove refractory sulfur compounds from diesel fuel. Applied Catalysis B: Environmental 63 (2008) 85-93.
6) Luis C., Jorge N. Aida G., Oxidative desulfurization of synthetic diesel using supported catalysts. Part II. Effect of oxidant and nitrogencompounds on extraction-oxidation process. Catalysis Today 118 (2008) 562-568.
7) Jae H., Xiaoliang Ma., Anning Z., Chunshan S., Ultra-deep desulfurization and denitrogenation of diesel fuel by selective adsorption over three different adsorbents: A study on absorptive selective mechanism. Catalysis Today 111 (2006) 74-83.
8) Sujit M., Yelda H. Larissa A., Oxidation of sulfur components in diesel fuel using Fe-TAML catalysts and hydrogen peroxide. Catalysis Today 116 (2006) 554-561.
9) Al Shahrani F., Xiao T., Llewellyn S., Barri S., Jiang Z., Shi H., Martinie G., Green M. Desulfurization of diesel via the H2O2 oxidation of aromatic sulfides to sulfones using tungstate catalyst. Applied catalyst B; Environmental 73 (2007) 311-316.
10) Shen, J.; Li, H.-P.; Zhao, H. Desulfurization by Oxidation/Adsorption Scheme over Ti3 (PW12O40) 4 Catalyst, Petroleum Science and Technology (2008), 26(18), 2182-2193.
11) Zhang, Shanshan; Zhou, Xinrui; Wang, Jing; Zhao, Defeng. One step catalytic oxidation of dibenzothiophene using t-butyl hydroperoxide over molybdenum oxide catalyst. Shiyou Yu Tianranqi Huagong (2008), 37(1).
12) Chan, Ngo Yeung: Lin, Ting-Yang; Yen, Teh Fu Superoxides: Alternative Oxidants for the Oxidative Desulfurization Process, Sonny Astani Department of Civil and Environmental Engineering, University of Southern California, Los Angeles, Calif., USA, Energy & Fuels (2008), 22(5), 3326-3328.
13) Constanti, Magda; Bordons, A.; Giralt, Jaume, Degradation of dibenzothiophene by *Pseudomonas putida*. Letters in Applied Microbiology (1994), 18(2).
14) Alves, Luis; Salgueiro, Rita; Rodrigues, Carla: Mesquita, Elsa; Mates, Jose; Girio, Francisco M. Desulfurization of dibenzothiophene, benzothiophene, and other thiophene analogs by a newly isolated bacterium, *Gordonia alkanivorans* strain 1B. Applied Biochemistry and Biotechnology (2005), 120(3), 199-208.
15) Wang, Lu-Cun; Liu, Qian; Huang, Xin-Song; Liu, Yong-Mei; Cao, Yong; Fan, Kang-Nian. Gold nanoparticles supported on manganese oxides for low temperature CO oxidation. Applied Catalysis, B: Environmental (2009), 88(1-2), 204-212.
16) Partition chromatography in the study of protein constituents, Gordon, A. H.; Martin, A. J. P.; Synge, R. L. M. Biochemical Journal (1943), 37 79-86.

17) Crystal structure of dibenzothiophene sulfone. Kronfeld, Louis R.; Sass, Ronald L. William Marsh Rice Univ., Houston, Tex., USA, Acta Crystallographies, Section B; Structural Crystallography and Crystal Chemistry (1968), 24(Pt. 7), 981-2.

18) Margaca, F. M. A.; Salvado, I. M. Miranda; Teixeira, J. Small angle neutron scattering study of silica gels; influence of pH. Journal of Non-Crystalline Solids (1999), 258 (1-3), 70-77.

19) C. J. Brinkera, K. D. Keefera, D. W. Schaefera, R. A. Assinka, B. D. Kaya and C. S. Ashley Sol-gel transition in simple silicates II Journal of Non-Crystalline Solids (1984) 63 (1-2) 45-59.

20) Effect of HCl in a two-step sol-gel process using TEOS. Huang, Wen Lai; Ling, Kai Ming; Gu, Shou Ren. Metal Division, Department of Materials Science and Engineering, Tsinghua University, Beijing, Peop. Rep. China. Journal of Non-Crystalline Solids (1999), 258(1-3).

21) C. J Brinkera, K. D Keefera, D. W Schaefera and C. S Ashley Sol-gel transition in simple silicates. Journal of Non-Crystalline Solids Volume 48, Issue 1, March 1982, Pages 47-64.

22) E. J. A. Popea and J. D. Mackenzie Sol-gel processing of silica: II. The role of the catalyst Journal of Non-Crystalline Solids Volume 87, Issues 1-2, 2 Oct. 1986, Pages 185-198.

23) Jackie Y. Ying † 1 Jay B. Benziger □‡ 1 Alexandra Navrotsky Structural Evolution of Alkoxide Silica Gels to Glass: Effect of Catalyst pH Journal of the American Ceramic Society Volume 76 Issue 10, Pages 2571-2582.

24) Kubo J., Higashi H., Ohmoto Y., Arao H., The additive effects of hydrogen-donating hydrocarbons derived from petroleum in hydrotreating of heavy oils. Nippon Oil Co. Ltd, cent. tech. res. lab., Naka-ku Yokohama-shi 231, JAPON.

25) Isao Mochida, Yui Moriguchi, Yozo Korai, Hiroshi Fujitsu and Kenjiro. Efficient liquefaction of Australian brown coal with a hydrogen-donating solvent under atmospheric pressure. Research Institute of Industrial Science Kyushu University, Fukuoka, Japan 812.

26) Catalysis by gold. Bond C. Geoffrey, Louis Catherien, Thompson T. David. Catalytic Science Series Vol. 6 Imperial College Press. Series Editor: Graham J. Hatchings.

27) Oxidation of dibenzothiophene by a metal-oxygen-aldehyde system. Dumont, V.; Oliviero, L; Mange, F.; Houaila, M. Laboratoire Catalyse et Spectrochimie, ENSI-CAEN, CNRS, Universite de Caen, Caen, Fr. Catalysis Today (2008), 130(1), 195-198.

28) Chemo and homoselective catalytic oxidation of sulfides to sulfoxides with supportednitric acid on silica gel and polyvinylpyrrolidone (PVR) catalyzed by KBr and/or NaBr. Zolfigol, Mohammad Ali; Amani, Kamal: Ghorbani-Choghamarani, Arash; Hajjami, Maryam; Ayazi-Nasrabadi, Roia; Jafari, Shila. Catalysis Communications (2008), 9(8), 1739-1744.

29) V-, Mo- and W-containing layered double hydroxides as effective catalysts for mild oxidation of thioethers and thiophenes with H2O2. Maciuca, Alina-Livia; Ciocan, Cristina-Elena; Dumitriu, Emil; Fajula, Francois: Hulea, Vasile, Catalysis Today (2008), 138(1-2), 33-37.

30) Oxidative desulfurization of dibenzothiophene catalyzed by Keggintype H3PMO12O40 and Na3PMo12G40. Qi, Guang-duo: Li, Xiang; Wang, An-jie; Han, Xing-hua; Wang, Gui-ru. State Key Laboratory of Fine Chemical, Dalian University of Technology, Dalian, Peop. Rep. China. Shiyou Xuebao, Shiyou Jiagong (2008), 24(6), 652-656.

31) Hon-hydrolytic synthesis of mesoporous silica-titania catalysts for the mild oxidation of sulfur compounds with hydrogen peroxide. Cojocariu, Ana Mihaela; Mutin, P. Hubert; Dumitriu, Emil; Fajula, Francois; Vioux, Andre; Hulea, Vasile. I Chemical Communications (Cambridge, United Kingdom) (2008), (42), 5357-5359.

32) Direct synthesis of mesoporous TiO2 and its catalytic performance in DBT oxidative desulfurization. Huang, D.; Wang, V. J.; Cui, Y. C.; Luo, G. S. Microporous and Mesoporous Materials (2008), 118(1-3), 378-385.

33) Carbon-based solid acid-catalyzed highly efficient oxidations of organic compounds with hydrogen peroxide, Shokrolahi, Arash; Zali, Abbas; Pouretedal, Hamid Reza; Mahdavi, Mohammad. Chemistry Department, Malek-ashtar University of Technology, Shahin-Shahr, Iran. Catalysis Communications (2008). 9(5), 859-863.

34) Oxidation of Dibenzothiophene and Desulphurization of Diesel. Ukkirapandian, V.; Sadasivam, V.; Sivasankar, B. Indian Additives Ltd., Chennai, India. Petroleum Science and Technology (2008), 26(4). 423-435.

35) Carbon-based solid acid-catalyzed highly efficient selective oxidations of sulfides to sulfoxides or sulfones with hydrogen peroxide. Zali, Abbas; Shokrolahi, Arash; Keshavarz, Mohammad Hossein; Zarei, Mohammad Ali. Acta Chimica Slovenica (2008), 56(2% 257-260.

36) Solvent Effect in Homogeneous and Heterogeneous Reactions To Remove Dibenzothiophene by an Oxidation-Extraction Scheme. Ramirez-Verduzco, L. F.; De los Reyes, J. A.; Torres-Garcia, E. Industrial & Engineering Chemistry Research (2008), 47(15), 5353-5361.

37) One step catalytic oxidation of dibenzothiophene using t-butyl hydroperoxide over molybdenum oxide catalyst. Zhang, Shanshan; Zhou, Xinrui; Wang, Jing; Zhao, Defeng. Shiyou Yu Tianranqi Huagong (2008), 37(1), 1-4.

38) Aerobic oxidative desulfurizatiom a promising approach for sulfur removal from fuels. Lu, Yong; Wang, Ya; Gao, Lida; Chen, Jinchun; Mao, Jiping; Xue, Qingsong; Liu, Ye; Wu, Haihong; Gao, Guohua; He, Mingyuan. ChemSusChem (2008), 1(4), 302-306.

39) Oxidation of Thiophene Derivatives with H2O2 in Acetonitrile Catalyzed by [Cp*2M2O5] (M=Mo, W): A Kinetic Study. Ciclosi, Marco; Dinoi, Chiara; Gonsalvi, Luca; Peruzzini, Maurizio; Manoury, Eric; Poli, Rinaldo. Organometallics (2008), 27(10), 2281-2286.

What is claimed is:

1. A method of extracting sulfur from an oxidized hydrocarbon feed, said method comprising the steps of:
    mixing a solution comprising a sulfur containing oxidized hydrocarbon feed, an acidified silica, a hydrogen donor solvent, any unreacted materials and reaction by-products with one or more polar organic solvents;
    allowing the sulfur containing oxidized hydrocarbon feed to migrate to the polar organic solvent phase; and
    removing the one or more polar organic solvents by evaporation to recover the sulfur.

2. The method of claim 1, wherein the oxidized hydrocarbon feed comprises asphaltenes, tar sands, bitumens, heavy petroleum or mixtures thereof.

3. The method of claim 1, wherein the hydrogen donor solvent is selected from the group consisting of hydrogen, natural petroleum, bases, alcohols, decahydronaphthalene, and tetrahydronaphthalene.

4. The method of claim 1, wherein acidified silica has a pH range from 0 to 2.

5. The method of claim 1, wherein the acidified silica comprises an amorphous silica or a silica gel.

6. The method of claim 1, wherein the polar organic solvent is selected from the group consisting of ethanol, methanol, n-propanol, isopropanol, n-butanol, formic acid, acetic acid, 1,4-dioxane, THF, dichloromethane, acetone, acetonitrile, DMF, DMSO, and any combinations thereof.

7. A sulfur extracted from a hydrocarbon feed by the method of claim 1.

8. A treated crude oil with reduced asphaltene content made by the method of claim 1.

9. A method for mid-distillate upgradation and sulfur removal in a fuel, said method comprising the steps of:
  mixing the fuel with a hydrogen donor solvent and an acidified silica to form a mixture; and
  oxidizing the sulfur in the mixture in air or a mixture of air and $O_2$ at a temperature between 50° C. and 210° C.

10. The method of claim 9, wherein the fuel comprises diesel, heavy petroleum, asphaltene, tar sands, bitumens, or mixtures thereof.

11. The method of claim 9, wherein the hydrogen donor solvent is selected from the group consisting of hydrogen, natural petroleum, bases, alcohols, decahydronaphthalene, and tetrahydronaphthalene.

12. The method of claim 9, wherein acidified silica has a pH range from 0 to 2.

13. The method of claim 9, wherein the acidified silica comprises an amorphous silica or a silica gel.

14. The method of claim 9, wherein the temperature for oxidizing the mixture is 120° C. to 160° C.

15. The method of claim 9, further comprising the step of adding a reduced noble metal catalyst or a mixture of a noble metal and one or more acidic catalysts, wherein the acidic catalysts comprise zeolites, silica, alumina or combinations thereof.

16. The method of claim 9, further comprising adding reduced gold, platinum, silver, and palladium metal nanoparticles or mixtures thereof.

17. The method of claim 9, wherein the silica comprises reduced gold, platinum, silver, and palladium particles or mixtures thereof.

18. The method of claim 9, wherein the solvents comprise at least one of decalin, tetralin, toluene, heptane, and dodecane.

19. The method of claim 9, wherein the method lowers the amount sulfur in the fuel by at least 90%.

20. The method of claim 9, wherein the fuel has less than 1,000, 500, 250, 200, 100, 50 or 10 ppm sulfur after treatment.

21. A fuel made by the method of claim 9.

* * * * *